US006833924B2

(12) United States Patent
Love et al.

(10) Patent No.: US 6,833,924 B2
(45) Date of Patent: Dec. 21, 2004

(54) DEVICE AND METHOD FOR TESTING TISSUE

(75) Inventors: Jack W. Love, Santa Barbara, CA (US); Robert W. Suggitt, Burnaby (CA)

(73) Assignee: Cardiomend, L.L.C., Santa Barbara, CA (US)

( * ) Notice: Subject to any disclaimer, the term of this patent is extended or adjusted under 35 U.S.C. 154(b) by 0 days.

(21) Appl. No.: 10/619,028

(22) Filed: Jul. 14, 2003

(65) Prior Publication Data

US 2004/0012792 A1 Jan. 22, 2004

Related U.S. Application Data

(63) Continuation of application No. 09/973,571, filed on Oct. 9, 2001, now abandoned, which is a continuation of application No. 09/591,005, filed on Jun. 9, 2000, now abandoned.
(60) Provisional application No. 60/138,953, filed on Jun. 11, 1999.

(51) Int. Cl.[7] ............................................. G01B 11/14
(52) U.S. Cl. ..................................................... 356/614
(58) Field of Search .......................... 356/601, 603–605

(56) References Cited

U.S. PATENT DOCUMENTS 5,706,815 A * 1/1998 Sarvazyan et al. .......... 600/438
6,144,199 A * 11/2000 Sharf et al. ................. 324/206

* cited by examiner

Primary Examiner—Zandra V. Smith
(74) Attorney, Agent, or Firm—Bryan Cave LLP

(57) ABSTRACT

An intraoperative tissue assessment device and method based on optical and mechanical techniques that allows a surgeon to assess certain mechanical properties of tissue samples. The device includes a cavity for housing and securing at least a portion of the tissue sample in communication with a pressurization source to inflate a portion of the tissue forming a dome of tissue having a height axis substantially perpendicular to the tissue sample secured within the cavity. The height of the dome of tissue along the height axis is generally proportional to the strength of the tissue sample. A source of illumination projects collimated light rays in the direction of the dome of tissue illuminating the dome of tissue and creating a Moiré fringe pattern, which may be used to determine the degree of anisotropy of the tissue sample when viewed through a viewing port arranged substantially directly above the dome of tissue.

1 Claim, 2 Drawing Sheets

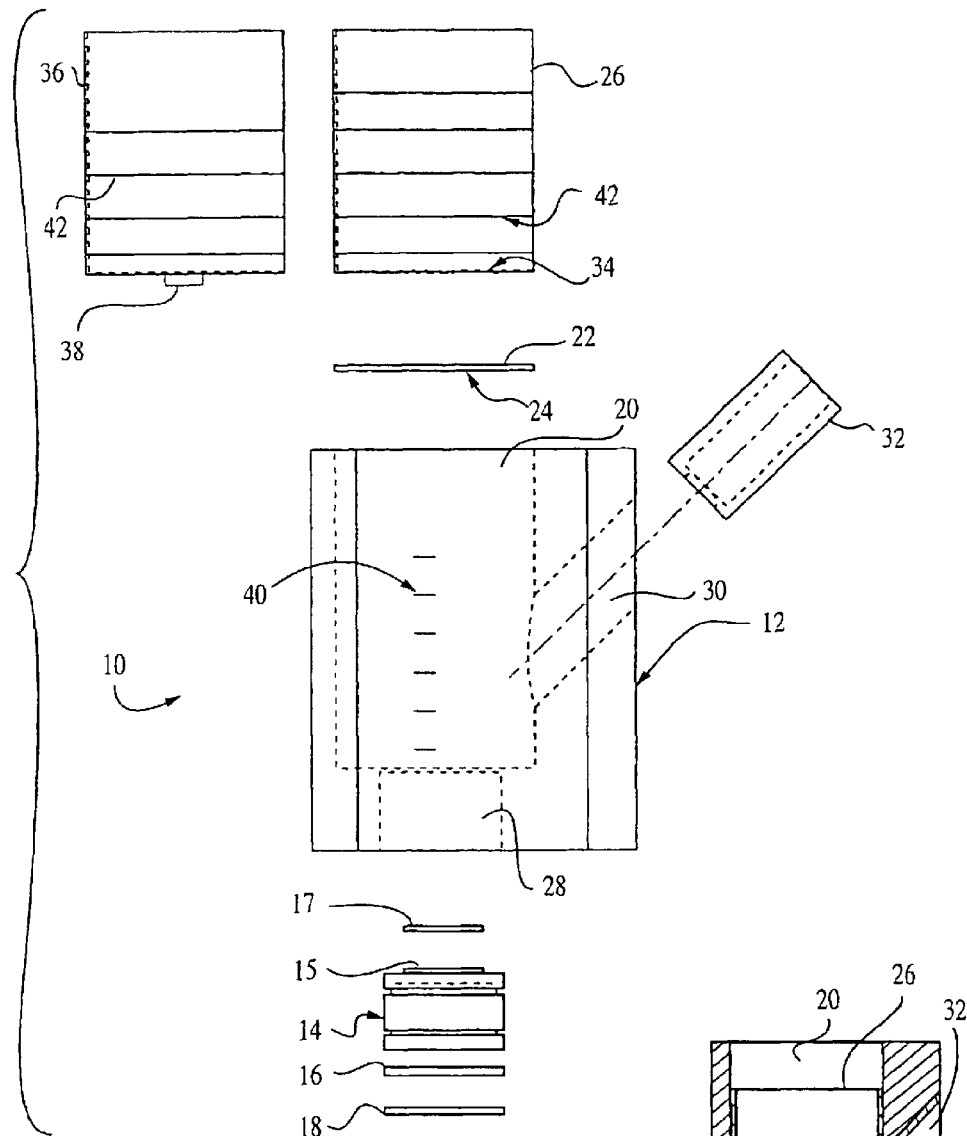
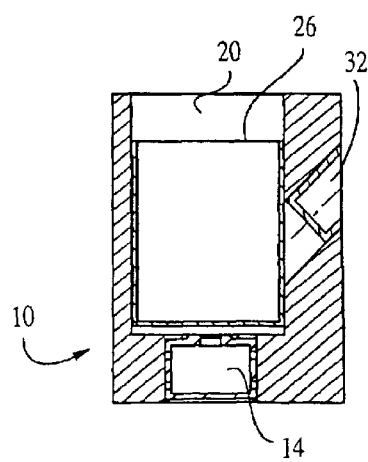
FIG. 2
FIG. 3

DEVICE AND METHOD FOR TESTING TISSUE

This application is a continuation of U.S. application Ser. No. 09/973,571, filed Oct. 9, 2001 now abandoned, which is a continuation of Ser. No. 09/591,005, filed Jun. 9, 2000 now abandoned, which claims the benefit of U.S. Provisional Application No. 60/138,953, filed Jun. 11, 1999.

FIELD OF THE INVENTION

The present invention relates generally to devices and methods for use in assessing various mechanical properties of tissue and, more particularly, to devices and methods for assessing autologous pericardium for potential use in repairing or reconstructing heart valves.

BACKGROUND OF THE INVENTION

The use of autologous tissue and particularly autologous pericardium for repair and reconstruction of heart valves is increasing. Surgeons involved in the use of autologous pericardium for valvular surgery, however, have reported a significant incidence of the need for re-operation. Although the need for re-operation has not been directly correlated to the use of defective pericardium, without sufficient pre-use testing of the tissue it is not possible to be certain that the quality of the pericardium has not been a factor in those patients who require re-operation for failed valves.

The use of pericardium in heart valve reconstruction requires that a two-dimensional tissue pattern be transformed into a three-dimensional semilunar valve, having a preferred trefoil pattern as disclosed in U.S. Pat. No. 5,719,399, the contents of which are hereby incorporated herein for all purposes. Additionally, pericardial reconstruction of a heart valve depends upon the biomechanical and physical properties of the tissue to ensure an appropriate strength and deformation of the leaflets during the normal cardiac cycle. Properties of crucial importance for ensuring normal valve action are thickness, tensile stiffness, and anisotropy. Anisotropy is the measure of stiffness of material as the material is pulled in two orthogonal axes. Materials that have equal stiffness in both axes are referred to as isotropic, while materials with statistically different values are referred to as anisotropic. The importance of tensile strength to valve action is obvious: the leaflets need to support peak pressure loading. Additionally, since each leaflet of the trefoil will be oriented 120 degrees from one another, the radial and circumferential strength of the tissue needs to be as uniform (i.e., isotropic) as possible to ensure equivalent action of each leaflet of the valve.

The gross appearance of the pericardium, and any past medical history of pericarditis or collagen disease, will form the basis of the surgical decision to use or not to use the patient's own tissue. Objective criteria, however, would greatly assist the decision making process. A knowledge of the basic mechanical properties of the pericardium may be helpful in identifying tissue that is not suited for valvular surgery. For example, if the tissue used in the reconstructed heart valve is too anisotropic, the leaflets may close asynchronously, affecting the functionality of the valve. Eliminating unsatisfactory pericardium before it is used might improve the success of valvular surgery with autologous tissue.

Conventionally, certain mechanical properties of tissue and similar structures were analyzed using uniaxial and/or biaxial test methods. Current laboratory methods and equipment, however, are not practicable for intraoperative use because the test equipment is overly large, requires regular maintenance and calibration, and because of the time required for conducting the tests. Additionally, it is generally impractical to run laboratory-type uniaxial tests in the operating room during a surgical procedure. Furthermore, uniaxial tensile tests, which were previously employed in many instances, are generally destructive to the tissue. Presently, surgeons desirous of using autologous pericardium face a significant challenge in incorporating quality control in the operating room where there are constraints imposed by time and the need for sterility.

The technique of inflating circular disks of tissue to investigate the anisotropy of the tissue has been demonstrated in the past. See, e.g., Zioupos, P., Barbenel, J. C., and Fisher, J., Mechanical and optical anisotropy of bovine pericardium, *Medical & Biological Engineering & Computing,* January 1992, 76–82; and Zioupos, P., Barbenel, J. C., and Fisher, J., Anisotropic elasticity and strength of glutaraldehyde fixed bovine pericardium for use in pericardial bioprosthetic valves, *Journal of Biomedical Materials Research,* Vol. 28, 49–57 (1994). The contents of both of these articles are incorporated herein for all purposes. However, the apparatus described therein to inflate the tissue and to determine the strength of the tissue were developed for use in the laboratory and are generally unsuitable for use in the operating room.

Accordingly, there is a continuing need for improved methods and devices for assessing various mechanical properties of tissue, such as pericardium that may be used for heart valve repair, reconstruction, or bioprostheses construction. A single preferred device would assess the thickness and strength of the tissue and would determine if it was isotropic or anistropic. Desirably, the novel device would be small, handheld, sterile, and disposable to allow for rapid measurement of these properties.

SUMMARY OF THE INVENTION

The present invention provides a self-contained device for evaluating mechanical properties of tissue. The device and methodology are based upon both optical and mechanical principles and are designed to measure, evaluate and assess critical mechanical properties of tissue, such as autologous tissue to be used for valvular repair or reconstruction. The compact, sterile, disposable handheld device is preferably designed to measure the thickness, strength and any inherent anisotropy of the tissue. The preferred method is non-destructive to the tissue.

The device measures the thickness of the tissue using a mechanical thickness float resting on a portion of the tissue. The float include reference marks that may be aligned with another set of reference marks on the device, forming a vernier scale. In order to assess tissue strength and isotropy, a portion of the tissue is secured within a small circular aperture and inflated. By noting the height of the inflated dome using a mechanical float and vernier scale, tissue strength can be determined. For evaluation of anisotropy, utilization of moiré fringe analysis, a conventional method of interferometry, is employed. Thus, while the tissue is inflated to form a dome, a collimated beam of light, offset from the tissue at approximately 45 degrees, illuminates the tissue. The illumination passes through a pattern of fine parallel lines, or Ronchi ruling. Illuminating and viewing the tissue through the ruling produces an interference pattern on the tissue that can be readily viewed. For a convex dome of a material with perfect isotropy, a pattern of concentric rings is observed. An anisotropic tissue will exhibit a pattern of oval or elliptical rings.

BRIEF DESCRIPTION OF THE DRAWINGS

To facilitate further discussion of the invention, the following drawings are provided in which:

FIG. 2 is an exploded side view of the tissue assessment device; and

FIG. 3 is a sectional view of the tissue assessment device showing the mechanical floats, pressure chamber, and illumination barrel inserted therein;

Figure 1:
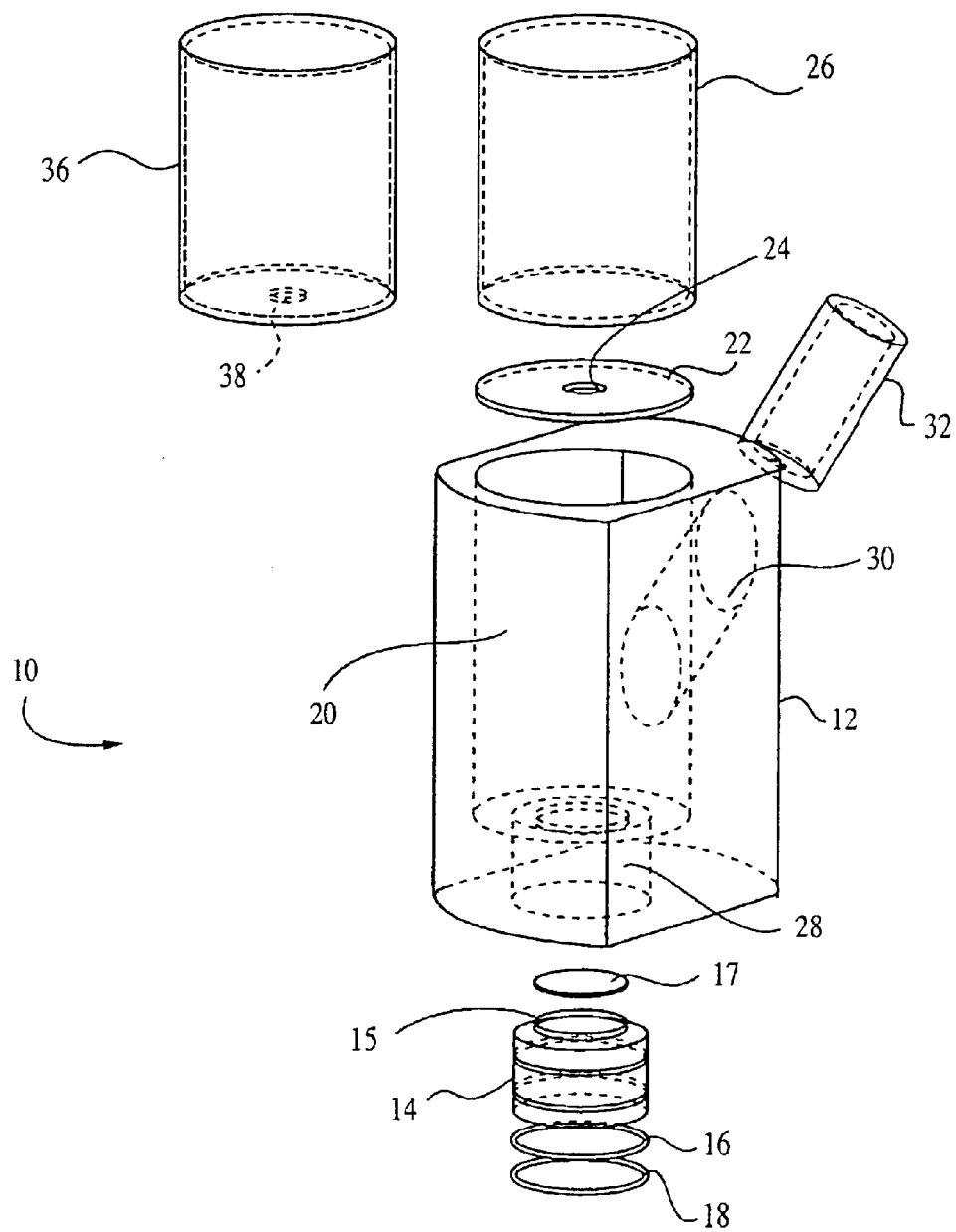
FIG. 1 is an exploded perspective view of the tissue assessment device of the present invention, illustrating the major components thereof.

These drawings are for illustrative purposes only and should not be used to unduly limit the scope of the claims.

DETAILED DESCRIPTION OF THE INVENTION

FIGS. 1, 2 and 3 illustrate the principle components of the presently preferred tissue assessment device 10, which may be used to determine the thickness, relative strength and degree of isotropy of a tissue sample 17. Preferably, the device 10 includes a body 12 that is integrally formed from an optically transparent material, for example, acrylic. As those skilled in the art are aware, acrylic is a solid, optically transparent material that does not distort collimated light traveling therethrough. The body 12 preferably houses a number of optical and mechanical components as described herein. The bottom portion of the body 12 includes a cylindrical hollow cavity 28 that houses a generally hollow pressure chamber 14 that holds the sample of tissue (not shown) in place and provides a means for inflating a portion of the tissue sample 17 into a convex dome. The pressure chamber 14 may be secured inside the hollow body using various conventional means. For example, the pressure chamber 14 may be threadedly attached to the body 12 inside the hollow cavity 28 using circumfrential grooves. Alternatively, the pressure chamber 14 may be held in place in the hollow cavity 28 using a thumb set screw.

A tissue sample 17 is placed upon the top of the pressure chamber 14 and the chamber 14 and sample are then inserted into the hollow cavity 28 of the device 10. The tissue sample 17 is clamped between the top of the pressure chamber 14 and the lower face of an orifice plate 22 located at the bottom of a float chamber 20. The tissue sample 17 itself provides the essential seal against the bottom of the orifice plate 22 while the O-rings 16 and 18 provide for a secondary seal when seated in the circumferential grooves on the pressure chamber 14.

The orifice plate 22 is preferably stainless steel, having a thickness in the range of 0.5–1.5 mm, and having an aperture 24 centrally located therein. The orifice plate 22 fixes the tissue sample 17 in place and allows the inflated dome of tissue dome to extend through the aperture 24 in the orifice plate 22 and physically contact the height float 26, as described below. Preferably, the aperture 24 in the orifice plate 22 is a small, substantially circular aperture (about 0.5 to about 2.5 cm in diameter) that permits the inflated tissue to inflate into a convex dome.

The tissue assessment device 10 may be used to measure the thickness of the tissue. A thickness float 36 having a cylindrical protuberance 38 may be inserted into the float chamber 20. The protuberance 38 loosely fits into the aperture 24 in the orifice plate 22 and in contact with the tissue sample 17 (uninflated). Preferably, the thickness float 36 is formed from an optically transparent material, e.g., acrylic. The cylindrical protuberance 38 is designed to be about 9.5 mm in diameter and about the same height as the orifice plate 22 (0.5–1.5 mm). The outside of the thickness float 36 includes reference marks 42 for a vernier scale designed to cooperate with reference lines 40 having a different scale on the body 12 of the device 10. The reference lines 40 on the body 12 of the device 10, which preferably extend over about three inches of the device 10, are designed in conjunction with the reference marks 424 on the height float 36 to magnify the height measurement and allow the measurement of tissue thickness to a resolution of about $\frac{1}{10}$ mm. The vernier scale reference marks may be etched into the acrylic thickness float 36 and body 12, or may be applied in other ways, such as, for example, a decal affixed using optically transparent adhesive.

The tissue assessment device 10 may also be used to determine the strength of the tissue sample 17. The top surface of the pressure chamber 14 includes one or multiple openings 15 for transmission of pressurization fluid to the portion of the tissue sample 17 positioned in the aperture 24 of the orifice plate 22. The tissue sample 17 may be placed under pressure by injecting pressurization fluid (e.g., saline) into the interior of the sealed pressure chamber 14. The pressurization fluid may be injected into the interior of the pressure chamber 14 via, for example, a conventional blood pressure bulb assembly or spring-loaded piston in communication with a port (not shown) in the side wall of the pressure chamber. Thus, a portion of the tissue sample 17 is incrementally pressurized and inflated into a convex dome of tissue. The dome of tissue is a section of a spheroid whose dimensions are determined by the diameter of a circle and the height of the dome. The dome of tissue has a height axis perpendicular to the plane of the tissue sample 17. The height of the dome of tissue measured along the height axis is substantially proportional to the strength of the tissue sample 17.

The assessment device 10 further includes an integrally formed cylindrical float chamber 20 designed to slideably receive a cylindrical height float 26. The height float 26 is preferably a lightweight, hollow cup-shaped piece of optically transparent material, such as acrylic. The height float 26 slides into the float chamber 20 and rests on top of, and mates with, the orifice place 22 (after the thickness float 36 has been removed from the float chamber 20). Thus, the orifice plate resides between the tissue sample 17 and the height float 26 and allows the height float 26 to contact the inflated dome of tissue. The height float 26 and the float chamber 20 are loose fitting, allowing the height float 26 to easily move vertically within the float chamber 20. Alternatively, the float chamber 20 may be filled with a saline solution surrounding the height float 26 to assist the height float 26 in easily moving within the float chamber 20 and provides superior optical properties for the transmission of collimated light rays.

The height float 26 is preferably used to measure the strength of the tissue sample 17 by measuring the height of the inflated dome of tissue. The outside of the height float 26 includes reference marks 42 for a vernier scale designed to cooperate with the reference lines 40 on the body 12 of the device 10. Thus, as the pressurization fluid causes a portion of the tissue sample 17 to inflate through the aperture 24 in the orifice plate 22 into a dome, the height float 26 will slide up within the float chamber 20. By using the vernier scale reference marks on the height float 26 and the body 12, the height of the dome of tissue may be ascertained. A relatively small movement in the height float 26 will move the reference lines 42 on the float 26 to align with another set of reference lines 40 on the body 12, allowing one to readily detect such small movements. The resolution of the vernier scale is preferably at least 1/10 mm. The vernier scale reference marks may be etched into the acrylic height float 26 and body 12, or may be applied in other ways, such as, for example, a decal affixed using optically transparent adhesive.

As an alternative embodiment, thickness float 36 and height float 26 may be combined into a single float with a protuberance 38 on one end. Thus, the end with the protuberance 38 may be inserted into the float chamber 20 to measure the thickness of the tissue sample 17. Then the float may be inverted to measure the height of the inflated dome of tissue.

The preferred tissue assessment device 10 may also be used to determine the degree of anistropy of the tissue sample 17. The body 12 of the device 10 includes an illumination chamber 30 that angularly extends from the exterior surface of the body 12 down into the float chamber 20 such that the central axis of the of the illumination chamber 30 and the central axis of the float chamber 20 intersect at the center of the orifice plate 22. The illumination chamber 30 houses an illumination barrel 32, which includes an illumination source and battery. The illumination source is preferably designed to produce collimated light rays, such as from a bright, 6V light emitting diode (LED), or, alternatively, from a incandescent source refracted through a collimating lens. The illumination chamber 30 is arranged at an angle of approximately 45 degrees such that the inflated dome of tissue is illuminated at approximately 45 degrees offset from the height axis of the dome of tissue. The illumination barrel 32 may be friction fit within the illumination chamber 30. The illumination chamber 30 may be slight conical shaped, i.e., it may be tapered such that the bottom of the chamber 30 is narrower in width than the top of the chamber 30 to hold the illumination barrel 32 in place. Alternatively, the illumination barrel 32 may be secured inside the illumination chamber 30 using, for example, a set screw.

The bottom interior or exterior of the height float 26 includes an overlay of parallel lines, commonly referred to as a Ronchi ruling grid 34. Preferably, the Ronchi ruling grid 34 contains fine opaque and transparent parallel line pairs, approximately 100 to the inch, with each line pair about 0.010 inches wide. The Ronchi ruling grid 34 may be applied as a decal using optically transparent adhesive or simply inserted as a friction fit into the hollow float. Illuminating the dome of tissue through the Ronchi ruling grid 34 produces a series of shadows upon the surface of the tissue. The surgeon or other member of the surgical staff may then view the sample from an angle coincident with the vertical axis of the height float through the Ronchi ruling grid 34 and observe an interference pattern which appears to be on the surface of the tissue sample 17. As is known, inflating a circular disk of isotropic membrane or tissue will generally produce a surface that is axisymmetic about its center point, i.e., a surface that has circular interference contours. Conversely, inflating a circular disk of anisotropic material will generally produce a surface that is not axisymmetric, i.e., a surface that will have oval or elliptical interference contours. A pattern consisting of concentric interference circles indicates that the tissue is isotropic, having equal strength in all directions. Anisotropic materials deform asymmetrically with an eccentric dome and the interference pattern will be more oval or ellipsoidal, with the weak axis defined by the longer axis of the ovals. Therefore, an interference pattern consisting of concentric ovals indicates anisotropy, with greater tissue strength in the direction of the short axis of the ovals. Thus, by viewing the shape of the interference contours through the height float 26, the surgeon can readily determine whether the tissue sample 17 shows variations in extensibility, which may lead to a decision to discard the particular tissue sample 17 from use in a replacement heart valve. Viewing the dome of tissue through the height float 26 allows for a clear and rapid assessment for the presence, direction and degree of anisotropy existent in the tissue sample 17.

The assessment device 10 may also include a second overlay grid consisting of several ellipsoidal planar curves placed to be used as comparison curves to assess the degree of anisotropy of the tissue sample 17. This second overlay grid may be placed on the bottom of the height float 26 and used to determine the degree of anisotropy to a maximal value, increasing the objectivity of the measurement and allowing the surgeon to make a quantitative decision on the acceptable degree of isotropy of the tissue sample 17. If the pattern viewed through the height float 26 show ovals outside of the reference curves, the tissue may be too anisotropic and should not be used for valve reconstruction. In practice, the pattern generated by viewing an inflated pericardium will rarely contain perfect circles. The pericardium tissue may still be acceptable provided that the length of the minor axis of the slightly ellipsoidal ovals is approximately 10% or less than the length of the major axis. Thus, the reference curves may be established based on this acceptable degree of tolerance.

The use of the presently preferred tissue assessment device 10 to assess the suitability of a sample of pericardium for use in a reconstructed heart valve may now be explained. The surgeon will remove a section of the pericardium, clean the surface of the tissue, treat the tissue using a solution of glutaraldehyde, and then cut the tissue into a conforming shape (as generally described in U.S. Pat. No. 5,719,399). A generally triangular remnant of the tissue sample 17 measuring approximately 1 inch on a side may then be used with the assessment device 10. The sample of tissue is placed upon the press chamber 14 and the chamber 14 is installed within the body 12. The thickness float 36 is then used to determine the thickness of the tissue. After determining the height of the tissue sample 17, the thickness float 36 is replaced with the height float 26. The pressure inside the chamber 14 is then increased, for example to 200 mm Hg, and a portion of the tissue sample 17 extends through the aperture 24 in the orifice plate 22 and contacts the lower surface of the height float 26. Assuming the sample of tissue is of minimal strength, the height float 26 will rise within the float chamber 20 and the surgical staff can then use the vernier scale reference markings to determine the distance traveled by the height float 26, which equates to the height of the dome of inflated tissue. By measuring the height of the inflated dome of tissue using the vernier scale, the relative strength of the tissue may be determined using the conventional LaPlace equation for membrane stress, $T=pr/2t$, where T is tension (strength), p is the pressure under which the dome of tissue is inflated, r is the radius of curvature of the dome of tissue (i.e., dome height), and t is the thickness of the tissue.

After completing the assessment of tissue strength, the surgical staff can use the tissue assessment device 10 for analysis of anistropy. While the tissue sample 17 remains inflated, the illumination source within the illumination barrel 32 is activated by, for example, using a switch to power the illumination source. The surgical staff can then view down through the top of the height float 26 to view the pattern of concentric rings or ovals through the Ronchi ruling grid 34. The pattern will indicate the degree of anistropy of the tissue.

The present method of inflating circular disk-shaped tissue samples and illuminating the domed surface to determine both the strength of the tissue sample as well as the degree of isotropy of the sample using a portable, sterile, pre-calibrated, hand-held, disposable, intraoperative device has wide applicability. The device assesses basic mechanical properties of autologous tissue to be used for valvular repair or reconstruction and may be used to discard tissue that is outside of an expected range of values for thickness, strength and anisotropy/isotropy. The device allows the cardiac surgeon to quickly and easily evaluate a patient's pericardium to determine its suitability for use in reconstructed or replacement heart valves in a rapid and practical manner. Once the device is manufactured, through appropriate quality control procedures, calibration can be set in the factory before shipping. After use, the device may be discarded, and the risks of calibration drift and viral transmission through re-use are eliminated.

We claim:

1. A surgical device for assessing the relative strength and degree of anisotropy of a tissue sample comprising:

a handheld body having a top portion and a bottom portion;

an upper chamber in the top portion of the body;

a lower cavity in the bottom portion of the body for housing a pressure chamber in fluid communication with a pressure source, the pressure chamber having a top portion having an opening for releasing pressure;

an orifice formed in the body between the upper chamber and low cavity providing fluid communication between the upper chamber and lower cavity and positioned such that the tissue sample can be secured within the lower cavity between the opening of the pressure chamber and orifice, such that fluid from the pressure source can pass through the opening in the pressure chamber and inflate the tissue forming a dome of tissue extending through the orifice having a height axis substantially perpendicular to the tissue sample secured within the cavity, wherein the height of the dome of tissue along the height axis is generally proportional to the strength of the tissue sample;

a source of illumination projecting collimated light rays in the direction of the dome of tissue illuminating the dome of tissue and creating a Moiré fringe pattern on the illuminated dome of tissue, wherein the Moiré fringe pattern may be viewed through the upper chamber and used to determine the degree of anisotropy of the tissue sample.

* * * * *